United States Patent [19]

Nathan et al.

[11] Patent Number: 4,863,732

[45] Date of Patent: Sep. 5, 1989

[54] INJECTABLE COMPOSITION FOR INDUCTIVE BONE REPAIR

[75] Inventors: Ranga Nathan, Newark; Andrea Thompson, Mountain View; Saeid Seyedin, Sunnyvale, all of Calif.

[73] Assignee: Collagen Corporation, Palo Alto, Calif.

[21] Appl. No.: 133,532

[22] Filed: Dec. 16, 1987

[51] Int. Cl.$^4$ .................. A61K 35/32; A61K 37/12; C07K 15/20; C12P 21/00

[52] U.S. Cl. ........................................ 424/95; 435/68; 435/69; 435/70; 435/268; 514/21; 514/801; 530/416; 530/417

[58] Field of Search ............................ 424/95; 514/21

[56] References Cited

U.S. PATENT DOCUMENTS

| | | | |
|---|---|---|---|
| 4,294,753 | 10/1981 | Urist | 530/395 |
| 4,394,370 | 7/1983 | Jefferies | 424/423 |
| 4,434,094 | 2/1984 | Seyedin et al. | 530/416 |
| 4,440,750 | 4/1984 | Glowacki et al. | 424/95 |
| 4,455,256 | 6/1984 | Urist | 530/350 |
| 4,563,350 | 1/1986 | Nathan et al. | 424/95 |
| 4,627,982 | 12/1986 | Seyedin et al. | 424/95 |
| 4,789,663 | 12/1988 | Wallace et al. | 514/21 |

OTHER PUBLICATIONS

Urist et al., (1982) Clinical Orthopaedics and Related Research 162:219-232.
Urist et al., (1984) Proc. Natl. Acad. Sci. U.S.A. 81:371-375.
Urist et al., (1983) Science 220:680-685.

Primary Examiner—John Kight
Assistant Examiner—Carlos Azpuru
Attorney, Agent, or Firm—Irell & Manella

[57] ABSTRACT

Aqueous suspensions of fibrillar atelopeptide collagen and osteogenic factor are effective injectable preparations for the repair of bone defects.

13 Claims, No Drawings

INJECTABLE COMPOSITION FOR INDUCTIVE BONE REPAIR

DESCRIPTION

1. Technical Field

The invention is in the fields of protein chemistry and osteoplasty. More particularly, the invention relates to an injectable preparation of fibrillar collagen and osteogenic factor that is useful for bone regeneration.

2. Background Art

Historically, the approach to repair of bones has evolved to greater and greater ability to supply a variety of compositions to replace missing bone material and to mediate the capacity of the bone cells to effect suitable repair. Prior workers have recognized that protein factors present in bone tissue are responsible for the maturation of bone progenitor cells into osseous tissue. Although these factors have not been totally identified and characterized heretofore, it has, on the basis of the presence or absence of such factors, been possible to classify preparations as either "conductive" or "inductive" depending on whether or not the preparations themselves supply these factors.

"Conductive" preparations lack osteogenesis factor (OF). They effect bone repair in a "passive" manner by providing a matrix for new growth. These compositions have taken a number of forms. Particularly relevant to the preparations of the present invention are bone repair compositions which consist essentially of some form of collagen, the organic structural material of bone. It appears that collagen matrices are able to provide the desired structure for the ingrowth of new bone into a defect. In practice, the matrix is placed into contact with mature bone cells capable of invading it and laying down a mineral network to complete bone growth; thus, the living tissue in contact with the matrix supplies any OF requirements. Indeed, the use of collagen itself, or of collagen mixed with hydroxyapatite, for this purpose has been reported widely over the last several years.

It would, of course, be desirable to provide a bone-healing matrix which not only passively conducts the intrusion of new bone tissue and subsequent mineralization, but also actively induces the conversion of osteoprogenitor cells into bone cells capable of effecting this repair, i.e., which effects "inductive" repair. The process of bone formation in vivo is complex and only partially understood, but appears to involve the intermediate formation of chondrocytes or cells capable of depositing cartilage, which chondrocytes are then replaced by cells capable of effecting mineralization. Materials which are capable of effecting such differentiation have recently been studied.

It is clearly understood that bone itself contains one or more factors which are involved in this process. Attempts have been made to purify whatever factors are responsible for this activity. A "bone morphogenic protein" (BMP) was extracted from demineralized bone using urea or guanidine hydrochloride and reprecipitated according to the disclosures in U.S. Pat. Nos. 4,294,753 and 4,455,256 to Urist. Urist subsequently reported (Urist, M. R., *Clin Orthop Rel Res* (1982) 162:219) that ion exchange purification of this crude protein mixture yielded an activity which was unabsorbed to carboxymethyl cellulose resin (CMC) at pH 4.8. Urist's reports in (*Science* (1983) 220:680-685 and *Proc Natl Acad Science* (U.S.A.) (1984) 81:371-375 describe BMPs having molecular weights of 17,500 and 18,500 daltons. Urist's most recent patent publication, EPA Publication No. 0212474, describes BMP fragments of 4,000 to 7,000 daltons obtained by limited proteolysis of BMP.

U.S. Pat. No. 4,434,094 to Seyedin and Thomas reported the partial purification of a bone generation-stimulating, bone-derived protein by extraction with chaotropic agents, fractionation on anion and cation exchange columns, and recovery of the activity from a fraction adsorbed to CMC at pH 4.8. This new protein fraction was termed "osteogenic factor" (OF) and was characterized as having a molecular weight below about 30,000 daltons.

Commonly owned U.S. Pat. No. 4,774,322, describes two proteins that were purified to homogeneity using a purification procedure that is similar in part to that disclosed in U.S. Pat. No. 4,434,094. Those two proteins eluted from CMC at about a 150-200 mM NaCl gradient. These two proteins were originally called cartilage-inducing factor (CIF) A and CIF B. CIF A was subsequently found to be identical to a previously identified protein called transforming growth factor beta (TGF-$\beta$). CIF B has been found to be a novel form of TGF-$\beta$ and is now known as TGF-$\beta$2. Neither has in vivo osteogenic activity per se.

Commonly owned U.S. Pat. No. 4,627,982 concerns a partially purified bone-inducing factor present in the CMC-bound fraction of U.S. Pat. No. 4,434,094 that elutes in the portion of the NaCl gradient below that in which the major portions of TGF-$\beta$ and TGF-$\beta$2 elute (i.e., below about 150 mM NaCl).

The availability of these specific inductive repair factors in crude or pure form has led to attempts to formulate preparations for implantation into bone defects. U.S. Pat. No. 4,440,750 discloses osteogenic compositions which include reconstituted collagen fibers and demineralized bone powder. The patent suggests formulating the mixture as an injectable but it is impractical if not impossible to deliver the mixture at practical concentrations via a syringe due to blockage of the needle by the bone powder particles. U.S. Pat. No. 4,394,370 (Jefferies) discloses compositions which include collagen of an undefined nature and either demineralized bone particles or a solubilized bone morphogenic protein, presumably that of Urist. The Jefferies material is described as a sponge suitable for implantation into a bone defect. Means for assessing the inductive effect of this implant were not described. U.S. Pat. No. 4,563,350 describes implant compositions which include OF extracts partially purified either by adsorption and release from CMC or by treatment of a low molecular weight fraction of the extract with an anion exchange resin at pH 7 and recovering the unbound fraction. These factors are administered in a collagen carrier which must include at least 5% by weight of a nonfibrillar form of collagen. These formulations were also constructed as solid bone implants.

U.S. Pat. No. 4,687,763 describes a solid implant for stimulating bone growth that is made by precipitating a demineralized bone extract onto a pliable collagen support. The preparation is effected by adding a solvent for the extractant solvent to the extract solution.

None of the foregoing compositions offers a practical injectable inductive preparation. The advantage of such an injectable preparation is that surgical procedures common with non-injectable inductive preparations could be avoided. The present invention relates to such a preparation of fibrillar collagen and at least partially purified OF.

DISCLOSURE OF THE INVENTION

The invention is directed to a novel injectable inductive preparation that can be conveniently used for bone repair both in humans and in other mammalian species. This preparation comprises, in its simplest form, an aqueous suspension of fibrillar atelopeptide collagen and at least partially purified osteogenic factor. The preparation may contain other active ingredients such as bone stimulating agents (such as TGF-$\beta$) or chemotactic agents that may facilitate osteogenesis. Such added materials should be such as to not destroy the injectability of the composition.

Methods for inducing bone growth at a predetermined site within the body of a living mammalian individual comprising injecting the preparation into the individual at the site are also part of the present invention.

The process by which a preferred embodiment of the preparation is made is yet another aspect of the invention. That process comprises the steps of:

(a) providing an acidic, aqueous solution of atelopeptide collagen and osteogenic factor;

(b) coprecipitating the atelopeptide collagen and osteogenic factor by increasing the pH of the solution; and (c) adjusting, if necessary, the concentration of the coprecipitate in the resulting suspension to about 5 to about 65 mg/ml, based on the atelopeptide collagen.

MODES OF CARRYING OUT THE INVENTION

A. Preparation of Collagen Component of the Solution

A collagen suitable for use in making an injectable preparation of the invention is an acidic aqueous solution of atelopeptide collagen. The preparation of such solutions of collagen is understood in the art, and commercial preparations, such as VITROGEN 100 collagen in solution (CIS) (Collagen Corporation, Palo Alto, Calif.) are available. Another collagen suitable for use in making an injectable preparation of the invention is a reconstituted fibrillar collagen which can be prepared by using CIS as a starting material, or by using commercial preparations, such as Zyderm ® Collagen Implant (ZCI) (Collagen Corporation, Palo Alto, Calif.). The collagen component is, however, not limited to any specific preparation, and the following represents a general outline of the procedure to obtain a suitable material. Any mammalian source may be used as long as the resulting collagen is highly purified, and is absent of the telopeptides, which are thought to be at least partly responsible for immunogenicity. Solubilization produces a purified form of collagen which also reduces immunogenicity.

In a suitable procedure, a mammalian skin preparation, preferably bovine skin, is softened by soaking it in a mild acid and then scraping it to remove hair, epidermis, and fat. The depilated skin is then soaked again in mild acid and ground or minced to form a finely divided preparation which is solubilized under nondenaturing conditions by dispersing it in an aqueous medium and digesting with a proteolytic enzyme other than a collagenase, preferably an enzyme that is active at low pH. Dilute acid solutions of, for example, HCl or carboxylic acids, such as acetic, malonic, or lactic acids, are used at low temperature with a pH normally in the range of 1.5–5, depending on the enzyme used. A preferred procedure is to disperse the comminuted tissue in HCl to a concentration of 1–5 g/l at a pH of about 2 at 20° C. After the tissue is dispersed, the enzyme is added and the mixture is incubated to permit the enzyme to digest the telopeptide and other solubilizable components of the tissue. Suitable enzymes for the digestion of the telopeptides which do not attack the triple helical portion of the collagen include pepsin, papain and trypsin, preferably trypsin, with an enzyme concentration in the range of 0.1%–10% by weight based on the collagen content of the tissue. The incubation period can last from about 2 days to 2 weeks and the process of solubilization may be monitored by determining the viscosity of the solution. Once the viscosity reaches a substantially constant level, the solubilization is complete, and the enzyme is deactivated and removed.

After denaturation of the enzyme, the solution is treated to remove the denatured enzyme and the digested portions of the tissue by various techniques, and combinations thereof including, for example, dialysis sedimentation, or filtration. The soluble components including the collagen are segregated from sedimented or filtered solids and concentrated, optionally fractionated on ion exchange chromatography, and further concentrated to produce a substantially pure atelopeptide collagen solution. Typical concentration levels of the collagen in the solution (CIS) are 3 to 25 mg/ml. The CIS may be reconstituted to a fibrillar form by neutralizing the solution at reduced temperatures, preferably about 10–25° C. preferably under hypotonic conditions relative to physiological ionic strength. The neutralizing solution may be added directly or, preferably, by dialysis of the solubilized collagen against it. Ionic strengths of about 0.03–0.1M, are used, and the pH is raised by adding an appropriate base or buffer such as disodium phosphate or sodium hydroxide to a level at which the collagen in solution reaggregates into fibrils. Fibril formation occurs under these conditions at a pH in the range of about 5–10, and the final pH is preferably in the range of 5–8. The duration of fibril formation is normally in the range of about one-half to 18 hours.

B. Preparation of Osteogenic Factor Component of the Solution

Partially pure demineralized bone extracts containing the factor or purified forms of the factor may be used. For instance, the partially purified factor described in U.S. Pat. No. 4,627,982 may be used. In this regard the term "at least partially pure" intends demineralized bone extracts of nonfibrous proteins as described below, preferably purified to at least the level described in U.S. Pat. No. 4,627,982. The partially purified factor can be further purified by precipitation in phosphate buffer at pH 6–8 by addition of 0.01–0.1M sodium phosphate. The precipitate is then redissolved in a non-ionic chaotropic agent and chromatographed on a hydroxyapatite column by HPLC. In any event, the procedure used to obtain the factor from bone is as follows.

The bone is first cleaned using mechanical or abrasive techniques, fragmented, and further washed with, for example, dilute aqueous acid preferably at low temperature, and then defatted by extraction with a lipophilic solvent such as ether or ethyl acetate. The bone is then demineralized by removal of the calcium phosphates in their various forms, usually by extraction with stronger acid. These techniques are understood in the art, and are disclosed, for example, in U.S. Pat. No. 4,434,094. The resulting preparation, a demineralized bone, is the starting material for the preparation of the claimed osteogenic protein.

The initial extraction is designed to remove the nonfibrous (e.g., noncollagenous) proteins from the demineralized bone. This can be done with the use of chaotropic agents such as guanidine hydrochloride (at least about 4 molar), urea (8 molar) plus salt, or sodium dodecylsulfate (at least about 1% by volume) or such other chaotropic agents as are known in the art (Termine et al, *J Biol Chem* (1980) 255:9760–0772; and Sajera and Hascall, *J Biol Chem* (1969) 244:77–87 and 2384–2396). The extraction is preferably carried out at reduced temperatures in the presence of a protease inhibitor to reduce the likelihood of digestion or denaturation of the extracted protein. Examples of protease inhibitors that may be included are phenylmethylsulfonylfluoride (PMSF), N-ethyl maleimide (NEM), benzamidine, and 6-amino hexanoic acid. The pH of the medium depends upon the extractant selected. The process of extraction generally takes on the order of about 4 hr to 1 day.

After extraction, the extractant may be removed by suitable means such as dialysis against water, preceded by concentration by ultrafiltration if desired. Salts can also be removed by controlled electrophoresis, or by molecular sieving, or by any other means known in the art. It is also preferred to maintain a low temperature during this process so as to minimize denaturation of the proteins. Alternatively, the extractant chaotropic agent need not be removed, but rather the solution need only be concentrated, for example, by ultrafiltration.

The extract, dissolved or redissolved in chaotropic agent, is subjected to gel filtration to obtain fractions of molecular weight in the range of about 20,000 to 35,000 daltons. Gel sizing is done using standard techniques, preferably on a Sephacryl S-200 column at room (10° C.–25° C.) temperature.

The sized fraction is then subjected to ion exchange chromatography using CMC at approximately pH 4.5–5.2 preferably about 4.8, in the presence of a nonionic chaotropic agent such as 6M urea. Other cation exchangers may be used, including those derived from polyacrylamide and cross-linked dextran; however cellulosic cation exchangers are preferred. Of course, as in any ion exchange procedure, the solution must be freed of competing ions before application to the column. The factor is adsorbed on the column and is eluted in an increasing salt concentration gradient in the range of about 10 mM to about 150 mM. This fraction is designated "CMB-1" for convenience. CMB-1 is desalted by dialysis or using a $C_{18}$ reversed phase column.

C. Preparation of the Compositions of this Invention

The compositions of the invention are conveniently prepared by coprecipitating CIS with OF or by simply admixing reconstituted fibrillar collagen with OF.

1. Coprecipitation

A preferred method for combining the fibrillar collagen and OF is by coprecipitation. An alternative, less desirable method is to mix the two components using mechanical mixers or homogenizers. The preferred coprecipitation procedure is as follows. The OF is solubilized, if necessary in acid, e.g., 0.01N HCl, pH 2.0, at concentrations in the range of about 3 µg/ml to 3 mg/ml. The CIS/OF mixture is coprecipitated by increasing the pH of the solution to about 6.5 to 8.5, preferably about 7 to 7.5. This is achieved through the addition of base, preferably 0.2M phosphate buffer, pH 11.2. The resulting precipitate is separated by centrifugation and resuspended at the desired concentration in an injectable vehicle. The concentration of coprecipitate in the suspension will normally be in the range of 5 to 65 mg/ml, preferably 10 to 25 mg/ml. The weight ratio of collagen to the at least partially purified OF will normally be in the range of 5:1 to 300:1.

2. Admixture

Suitable preparations for an admixture of injectable collagen and OF is variable, as the concentration of one influences the permissible range for the concentration of the other. It is therefore preferable to consider the parameters which are required in the final composition. For injectability, the reconstituted fibrillar collagen may be present in the range of 5–65 mg/ml, preferably 10–20 mg/ml. A reconstituted collagen suspension having a greater collagen concentration may be used if it is mixed with a solution of OF that would result in a dilution of the collagen concentration. The weight ratio of collagen to the partially pure OF in the admixture will be as indicated above.

As indicated previously, either additional inactive materials or bioactive materials may be added to the preparation. Such added materials should be such as do not destroy the injectability of the composition.

E. Modes of Administration

The compositions of the invention are prepared as injectables. They are administered to the defect by conventional modes of injection known to the practitioners of the art. In this regard, the compositions are conveniently packaged in syringes for convenient sterile administration. The composition should be stored before use at low temperature, such as approximately 4° C. and administered in an amount depending on the size of the defect and the intended role of the compositions in curing the defect.

EXAMPLES

The following examples further illustrate the invention. These examples are not intended to limit the invention in any manner.

EXAMPLE 1

Partially purified CMB-1 fraction was prepared from bovine bone powder as described in U.S. Pat. No. 4,563,350. Briefly, metatarsal bovine bone was demineralized in 0.5N HCl and dissociatively extracted with 4M guanidine hydrochloride (GU.HCl). The GU.HCl extract was concentrated and passed through a gel filtration column (S-200) to obtain the low molecular weight proteins (<35K daltons). The low molecular weight proteins were further concentrated, desalted on a GH-25 column and loaded on a cation exchange column (CM-52) to obtain the CMB-1 fraction. The CMB-1 proteins were desalted finally on a reversed phase HPLC column (C18) and directly lyophilized.

CMB-1 proteins were coprecipitated with collagen as follows. All procedures were performed under a laminar flow hood. Lyophilized CMB-1 was solubilized in 0.01N HCl (pH 2.0) at approximately 2.5 mg/ml protein concentration. The solution was sterile filtered through a 0.22 µm filter and combined with VITROGEN ®100 CIS (3 mg/ml). The mixture was stirred for about 5 min to ensure complete mixing. Coprecipitation of the CMB-1 proteins and the collagen was achieved by adding 1 part of 0.2M phosphate pH 11.2 to 9 parts of the solution. The mixture was stirred for approximately 5 min and left in the hood for a period of about 18 hours. The precipitate, a mixture of CMB-1 proteins and fibrillar collagen (FC) was separated from the supernatant by centrifugation at 12,000 RPM for 20 min. The supernatant was preserved for protein determination. The precipitate was retrieved and the wet weight determined. Based upon previous observations it is expected that approximately 85% of the total collagen protein precipitates from CIS in the form of FC. The FC concentration is adjusted to 15 mg/ml in 0.13M NaCl, 0.02M sodium phosphate using the supernatant and 1.3M NaCl, 0.02M sodium phosphate, pH 7.2, as a medium for diluting the precipitate. The FC/CMB-1 complex was homogenized between syringes to ensure complete mixing. The homogenized sample was subsequently loaded into 1 cc syringes and stored in cold (4° C.) until use.

The ability of FC/CMB-1 coprecipitate to induce endochondral bone formation in mammals was determined as follows. Sprague-Dawley rats (34-40 day-old males) were injected subcutaneously with 0.2 cc of the FC/CMB-1 mixture on either side of the ventral thoracic region. Samples of FC alone without the CMB-1 were also injected as negative controls. Explants were removed at 7 and 14 days and evaluated biochemically and histologically for cartilage and bone formation.

The histological scores are summarized in Table 1 below.

TABLE 1

| Group | 7 Day Implant | | 14 Day Implant | |
|---|---|---|---|---|
| | Cartilage | Bone | Cartilage | Bone |
| FC/OF | 4+ | 2+ | 2+ | 4+ |
| FC Control | 0 | 0 | 0 | 0 |

Histologically, formulations comprising the coprecipitate showed extensive cartilage induction by 7 days of implantation. There was also evidence of early bone formation around the periphery of the implant at this time point. Consistent with this observation was an increase in alkaline phosphatase (AP) activity in these implants (approximately 35 units AP/g explant). Control injections of FC samples did not show any biological activity. By 14 days, all FC/CMB-1 implants showed increased levels of bone formation with a moderately well differentiated bone marrow. Cartilage activity was either absent or confined to the central portions of the implant at very low levels. Histologically the implants showed no signs of inflammation indicating compatability of the implants to the host tissue.

EXAMPLE 2

A coprecipitate was prepared and tested as in Example 1 except that more highly purified osteogenic protein (purified through ConA affinity chromatography as described above) was used in place of CMB-1 protein.

Results were similar to those obtained in Example 1 with the explants containing the coprecipitate showing extremely high bone induction activity.

EXAMPLE 3

Zyderm Collagen Implant (ZCI) 'material at 65 mg/ml was diluted with 20 mM phosphate, pH 7.4, 0.13M NaCl to a concentration of 35 mg/ml. The diluted collagen was mixed throughly with the CMB-1 proteins, described in Example 1, to a final collagen concentration of 30 mg/ml with 1.2 mg/ml of CMB-1 protein. The percentage of OF in this composition is about 3.8%. The admixture was then loaded into 1 cc syringes and stored at 4° C. until injection.

The ability of ZCI/CMB-1 admixture to induce endochondral bone formation in mammals was determined as follows. Four young, male Sprague-Dawley rats were injected subcutaneously with 0.5 cc ZCI/CMB-1 on either side of the ventral thoracic region of each rat. Reconstituted demineralized bone (R-DBP), as described in U.S. Pat. No. 4,563,350 and ZCI, alone, served as controls. Control injections of ZCI were made using 0.5 cc of ZCI and control samples of R-DBP (40 mg) were implanted surgically.

Explants were removed at 14 and 28 days and were evaluated biochemically and histologically for cartilage and bone formation. Histological evaluation was made after fixing, sectioning, and staining using standard procedures. Biochemical evaluation was made by assaying for cartilage proteoglycan content and alkaline phosphatase specific activity.

Histological evaluation was based on cartilage induction, bone formation, vascularization, and fibroblast invasion. By these criteria, the collagen vascularization and fibroblast invasion after 28 days, but not at 14. Both the ZCI/CMB-1 composition and R-DBP composition showed activity based on all four criteria, although that of R-DBP was slightly more uniform and greater than that exhibited by the ZCI/CMB-1 composition.

Proteoglycan activity assayed after 14 days was zero for the ZCI alone and was 550 mg C-PG/g wet tissue for ZCI/CMB-1 and 1300 mg C-PG/g wet tissue for the R-DBP.

Alkaline phosphatase activity was assayed after 14 days and 28 days; again, explants from animals injected with ZCI alone showed essentially no alkaline phosphatase activity; the explants from rats injected with ZCI/CMB-1 showed 8.5 U AP/g wet tissue after 14 days and 14.5 U AP/g wet tissue 28 days. The corresponding alkaline phosphatase activity for the explants from rats injected with R-DBP were 12 U/g at 14 days and 20 U/g at 28 days.

Accordingly, it can be concluded that injectable, admixed ZCI/CMB-1 compositions are capable of bone formation-stimulating activity comparable to that exhibited by the R-DBP preparations.

Modifications of the above described modes for carrying out the invention that are obvious to persons of skill in the fields of protein chemistry and osteoplasty are intended to be within the scope of the following claims.

We claim:

1. An injectable bone growth-inducing composition comprising an injectable aqueous suspension of fibrillar atelopeptide collagen and at least partially purified osteogenic factor, wherein the fibrillar atelopeptide collagen and the at least partially purified osteogenic factor are in the form of a coprecipitate.

2. The composition of claim 1 wherein the concentration of collagen is in the range of about 5 to about 65 mg/ml.

3. The composition of claim 2 wherein the weight ratio of collagen to osteogenic factor in the coprecipitate is in the range of about 5:1 to 300:1.

4. The composition of claim 4 wherein the osteogenic factor is coprecipitated from an acidic demineralized bone extract.

5. A method of inducing bone growth at a predetermined site within the body of a living mammalian individual comprising injecting the composition of claim 1 into said individual at said site.

6. A method of inducing bone growth at a predetermined determined site within the body of a living mammalian individual comprising injecting the composition of claim 2 into said individual at said site.

7. A method of inducing bone growth at a predetermined site within the body of a living mammalian individual comprising injecting the composition of claim 3 into said individual at said site.

8. A method of inducing bone growth at a predetermined site within the body of a living mammalian individual comprising injecting the composition of claim 4 into said individual at said site.

9. The method of claim 5 wherein the individual is a human.

10. A process for making the composition of claim 4 comprising the steps of:
    (a) providing an acidic, aqueous solution of atelopeptide collagen and osteogenic factor;
    (b) coprecipitating the atelopeptide collagen and osteogenic factor by increasing the pH of the solution; and
    (c) adjusting, if necessary, the concentration of the coprecipitate in the resulting suspension to about 5 to about 65 mg/ml, based on the atelopeptide collagen.

11. The process of claim 10 wherein the osteogenic factor is present as a demineralized bone extract.

12. The process of claim 11 wherein the weight ratio of atelopeptide collagen to demineralized bone extract in the solution is about 5:1 to 300:1.

13. The process of claim 10 wherein the pH of the solution is increased to about 6.5 to about 8.5.

* * * * *